(12) United States Patent  
Heikkilä

(10) Patent No.: US 6,411,841 B2  
(45) Date of Patent: Jun. 25, 2002

(54) HUMAN-RELATED MEASURING ASSESSMENT

(75) Inventor: Ilkka Heikkilä, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/792,268

(22) Filed: Feb. 23, 2001

(30) Foreign Application Priority Data

Feb. 23, 2000 (FI) .............................................. 20000417

(51) Int. Cl.⁷ .................................................. A61B 5/02
(52) U.S. Cl. ....................................................... 600/513
(58) Field of Search ................................. 600/300, 520, 600/519, 513

(56) References Cited

U.S. PATENT DOCUMENTS 5,738,612 A   4/1998   Tsuda
5,782,772 A   7/1998   Stegmann
5,810,722 A   9/1998   Heikkila
5,853,351 A   12/1998  Mauro et al.

FOREIGN PATENT DOCUMENTS

EP   0 947 160 A1   10/1999
JP   9038051        2/1997

OTHER PUBLICATIONS

T.L. Talbot, et al., "Nonivasive Detection of the Anaerobic Threshold During Computer–Controlled Exercise Testing", Med. & Biol. Eng. & Comput., vol. 23, pp. 579–584 (1985).

Primary Examiner—Scott M. Getzow
(74) Attorney, Agent, or Firm—Hoffmann & Baron, LLP

(57) ABSTRACT

A heart rate measuring arrangement which comprises measuring means (410A to 410B) for measuring heart rate information, forming means (452) for forming an assessment of the lactate concentration in the body on the basis of the measured heart rate information, and presenting means (450) for presenting the formed assessment of the amount of lactate in the body.

37 Claims, 7 Drawing Sheets

HUMAN-RELATED MEASURING ASSESSMENT

BACKGROUND OF THE INVENTION

1. Field of the Invention

The invention relates to exercise and sports, and in particular, to applications in which lactate concentration is assessed in a human body in connection with exercise.

2. Brief Description of the Related Art

Efficiency of an exercise can be described as exercise intensity in relation to time, which intensity can be observed e.g. as heart rate frequency in relation to time. When momentary intensity of exercise is observed in this manner, a momentary assessment of stress is obtained. The effect of long-term exercise stress depends on the individual such that a person having good condition endures exercise stress better than a person having poor condition. For instance, it is possible that each one is able to perform the same exercise at the same intensity, but the individual effect of the exercise is different: the person having good condition is not liable to considerable fatigue, whereas the person having poor condition performs the same exercise at the extreme limits of capacity. The effect of the momentary stress on the individual and on the individual stress level experienced during exercise depends on preceding stress.

In training, it is important to know the amount of cumulative stress, which increases under hard stress and decreases at rest. Concentration of lactate, i.e. lactic acid, in blood represents well the cumulative stress. The amount of lactate is the only indicator by which the cumulative stress can be measured in practice. Recovery after exercising is important both to metabolism and to muscle care. Stress pain resulting from exercising can be reduced significantly by well-performed recovery exercise, whereby recovery is achieved in shorter time and the capability of the muscles and the system to perform the next exercise improves substantially. The most important function of the recovery exercise is to remove the accumulated lactic acid, i.e. lactate, if any, from the body quickly and efficiently, so that the lactate could not cause pain or post-stress conditions in the muscles. This calls for a method by which the amount of lactate can be assessed in the body on a continuous basis.

According to the prior art, the amount of lactate can be measured by taking a blood sample that is analyzed. The prior art has disadvantages. The measurement of lactate from blood is painful, discrete, slow and often requires a complicated measuring arrangement.

SUMMARY OF THE INVENTION

The object of the invention is to provide an improved method for assessing lactate concentration in the body. This is achieved by the method to be described in the following. The method concerns assessing the lactate concentration in the human body in connection with exercise. The method measures a person's heart rate information in the form of one or more heart rate parameters to be included in a mathematical model as input parameters and, by means of a mathematical model which models the lactate concentration in the body, forms a lactate concentration level of the person's body as an output parameter of the model to be presented in the assessment of the lactate concentration of the body.

The invention also relates to a heart rate measuring arrangement. The heart rate measuring arrangement comprises measuring means for measuring heart rate information, forming means for forming an assessment on the basis of the measured heart rate information of the lactate concentration of the body, presenting means for presenting the formed assessment of the amount of lactate in the body.

The preferred embodiments of the invention are disclosed in the dependent claims.

The invention thus relates to a method and equipment for assessing lactate, i.e. lactic acid, in the body. The method of the invention is advantageously implemented by means of a mathematical model. In the description of the invention, the mathematical model refers to a plurality of mathematical operations and rules, by which output parameter values are obtained from input parameter values. Mathematical operations include e.g. arithmetical operations, such as addition, subtraction and multiplication. It is also possible to implement the mathematical model as a table or a database, whereby an output parameter value corresponding to a given input parameter value is read directly from the database. The model may include a plurality of submodels, but it is obvious that the invention is not restricted to how many submodels the model comprises. In one embodiment of the invention, the mathematical model is a neural network, but the invention is not restricted thereto, however.

The input parameters of the model include one or more heart rate parameters representing the person's heart rate, such as the heart rate calculated from heart beat frequency, standard deviation of the heart rate, change rate of the heart rate or a similar parameter that can be calculated from the heart rate. According to one embodiment, the input parameters of the model also include one or more physiological parameters which refer to the person's age, weight, height, gender or other physiological property. In one preferred embodiment, the model's input data comprises one or more stress parameters, such as the runner's speed, resistance of an exercise bike or activity measured with an acceleration transducer or the like. By means of the heart rate and physiological parameters it is possible to provide an assessment of the person's physical condition, for instance, on the basis of the maximal oxygen uptake. According to one preferred embodiment of the model, a user's stress level during exercise is formed on the basis of the heart rate information and optionally the stress and user information, on the basis of which stress level the lactate amount in the body is assessed. Then there is no direct correlation between the heart rate information and the lactate, but the connection is formed through a stress level definition, which stress level can be represented by a quantity of performed intensity during the last hour.

In connection with the present description of the invention, an exercise, i.e. sporting performance, refers to a physical performance, at least part of which is carried out at a workload level exceeding the anaerobic level, whereby lactate is accumulated in the muscles of the person's body. Lactate concentration can also be assessed for a given period of time, for instance, for a few hours before and after the exercise, so the application of the invention is not only restricted to the moment of exercise. It can be assumed that the exercise divides into the following phases: warm-up, active phase, recovery phase when the exercise is preceded and followed by a rest. Different phases can be defined and distinguished, for instance, on the basis of heart rate levels and/or workload levels. Then, for instance, the recovery phase can be defined as a performance level when the heart rate is dropped from 130 beats per minute to a resting level of 70 beats per minute.

In the solution of the invention for assessing the lactate concentration in the body, the person whose lactate concentration is to be monitored advantageously wears a heart rate monitor. The heart rate monitor is a device employed in sports and medicine, which measures human heart rate information either from an electrical impulse transmitted by the heart or from the pressure produced by the heart beat on an artery. Generally, the heart rate monitors have a structure comprising an electrode belt to be fitted around the user's chest measuring the heart rate by means of two or more electrodes. The electrode belt transmits the measured heart rate information inductively as one or more magnetic pulses per heart beat, for instance, to a wrist-worn receiver unit. On the basis of the received magnetic pulses, the receiver unit calculates the heart rate and, when needed, other heart rate variables, such as moving standard deviation of the heart rate. Often, the receiver unit, i.e. the wrist monitor, also comprises a display for displaying the heart rate information to the exercise performer and a user interface for the use of other facilities of the heart rate monitor. In the above-described situation, the heart rate monitor refers to the whole formed by the electrode belt and the receiver unit. The heart rate monitor can also be a one-piece device, i.e. such that also the presenting means are located on the chest, whereby there is no need to transmit the information to a separate receiver unit. Further, the structure of the heart rate monitor can be such that it only comprises a wrist-worn monitor which operates without the electrode belt to be fitted around the chest measuring the heart rate information from the vessel pressure. In the description of the invention, the heart rate measuring arrangement refers to the above-described heart rate monitor solutions. The heart rate measuring arrangement also comprises the solutions, in which heart rate information is transmitted to an external computer or to a data network, which has presenting means, such as a computer screen, for presenting the information measured or generated by the heart rate monitor.

According to the invention, one or more mathematical models and other functions required by the model are advantageously implemented by means of software for a general-purpose processor of the heart rate monitor. The models and functions can also be implemented as ASIC, with separate logic components or in another, corresponding manner. In a preferred embodiment of the invention, the heart rate monitor comprises entering means for entering input parameters. The input parameters to be entered include, for instance, the user's physiological parameters and stress parameters representing the workload of the exercise. The entering means can be, for instance, a keypad of the heart rate monitor, display equipment that supports control, speech control, a telecommunication port for external control or the like. The heart rate monitor also advantageously comprises a display for displaying the lactate concentration to the user, exercise instructor, trainer, doctor or the like. Instead of the display, the lactate concentration can be communicated also e.g. by speech control, via a telecommunication port for transmitting the information to an external device, such as computer, or in another corresponding manner. In one embodiment, the lactate concentration during exercise can be stored in a memory of the heart rate monitor, wherefrom the information can be outputted afterwards.

An advantage of the invention is non-invasiveness, i.e. when assessing the lactate concentration there is no need to take blood samples, which is painful and slow and hampers the performance of exercise. By means of the invention, the amount of lactate in the body can be monitored on a continuous basis as compared with prior art methods, whereby discrete evaluations of the lactate concentration are obtained. By means of the invention, it is further possible to adjust the workload of the exercises to a level which is optimal for the lactate to accumulate in the body and to be removed from the body.

BRIEF DESCRIPTION OF THE DRAWINGS

In the following, the invention will be described in greater detail with reference to the attached drawings, wherein.

DETAILED DESCRIPTION OF THE PREFERRED EMBODIMENTS

Figure 1:
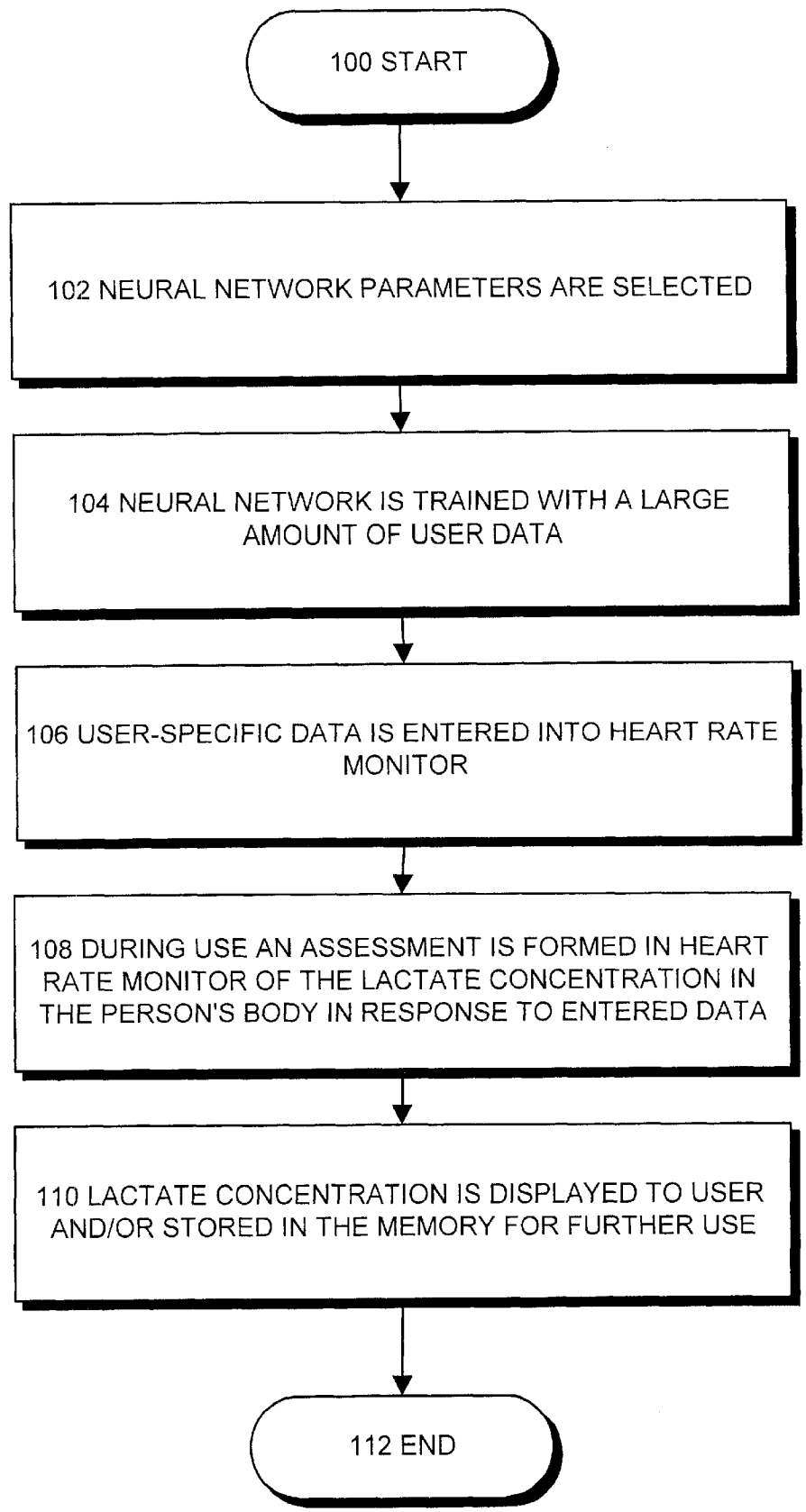
FIG. 1 shows a preferred embodiment of the method of the invention.

In the following, the invention will be described by means of preferred embodiments with reference to the attached drawings 1 to 4C. FIG. 1 describes one preferred embodiment of the invention. At step 102, a mathematical model is formed, the purpose of which model is to define and monitor the amount of lactate in the body by means of one or more heart rate parameters. The heart rate parameter refers, for instance, to the heart rate calculated from the heart beat frequency, the standard deviation of the heart rate or like parameter calculable from the heart rate. According to one embodiment, the model includes as an input parameter one or more physiological parameters, which refer to the person's age, weight, height, gender or other parameters representing the person's physiological properties. In one preferred embodiment, the model includes, as data to be entered, one or more stress parameters, such as the runner's speed, the exercise bike's resistance or activity measured with an acceleration transducer or the like. By means of the heart rate and physiological parameters it is possible to evaluate the user's physical condition, for instance, on the basis of the maximal oxygen uptake. According to one preferred embodiment of the model, the user's exercise stress level is formed on the basis of the heart rate information and optionally the workload and user information and on the basis of the exercise stress level the amount of lactate in the body is assessed. There is no direct correlation between the heart rate information and the lactate, but the connection is formed through a stress level definition, which stress level can be described by a quantity of performed intensity during the last hour. In this exemplary embodiment the model is preferably a two-part mathematical model, in which the first part output, i.e. the exercise stress level, is used as an input for the second part. Apart from the lactate concentration, one embodiment has the exercise stress level as a model output parameter presented by values between 1 to 100. On the basis of the exercise stress level it is thus possible to assess how the exercise succeeded and to use the exercise stress level for planning the exercise program, for instance, such that on the basis of the exercise stress level the heart rate during exercise, the running speed or the resistance of the exercise bike are inversely controlled. An advantage is achieved by adding the above-described input parameters that the lactate assessments provided by the model are more accurate as the model becomes more versatile. In one preferred embodiment, the mathematical model according to the above-described embodiments is a neural network which is particularly well applicable to complex biological modelling situations. A physiological background for the model is provided by known physiological intercorrelations in generating lactate, which will be discussed below in view of the basis of the model.

Carbohydrates, fats and protein mainly constitute human energetics. Their consumption and proportion depend on the condition of the body, available amount of nutrients and intensity of exercise. Carbohydrates from food provide glucose which is stored in muscles as glycogen. In glycolysis glucose degrades and releases energy. The reaction may take place either aerobically or anaerobically.

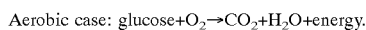

Aerobic case: glucose+$O_2$→$CO_2$+$H_2O$+energy.

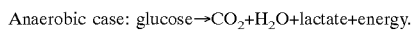

Anaerobic case: glucose→$CO_2$+$H_2O$+lactate+energy.

In addition to the above carbohydrate degradation, there are corresponding degradation equations for the degradation of fatty acids and protein, however, it is not relevant to present them in this context. Degradation of fatty acids into energy can only take place aerobically. In a muscle, oxidation of fatty acids into energy requires simultaneous burning of glucose. The muscles obtain the energy needed for exercise from adenosine triphosphate (ATP). ATP deficiency resulting from exercise should be replenished by producing new ATP from the energy reserves. For the first 10 to 15 seconds as the exercise stress starts, creatine reserves constitute a sufficient source of energy for producing ATP required by the muscles. Thereafter, it is possible to consume energy obtained from the glucose in the body. Utilization of fatty acids is not possible until 15 minutes after the onset of exercise stress. Energy production is always mainly aerobic in a maximal exercise stress of short, lasting tens of seconds. In an exercise stress of a few seconds energy is produced mostly by alactic processes by means of creatine phosphate. However, the creatine phosphate reserves are small and after ten seconds of exercise stress energy is already produced mostly by lactate-forming processes. In a maximal exercise stress of longer duration, lasting minutes, the proportion of aerobic energy production increases. However, the long-term stress employs nearly the same energy production mechanisms as the short-term stress.

The amount of lactate, i.e. lactic acid, is a balance reaction in the body, i.e. lactate is produced and removed at rest a small but equal amount. If the workload increases, more lactate is produced, but the lactate removal mechanisms also start working at a higher rate. If the stress does not rise to a very high level, the lactate removal mechanisms are capable of removing the lactate at the same rate with production. However, the removal mechanisms have a limited reaction rate, and consequently the amount of lactate is greatly affected by the nature of the workload. Proportionally, more lactate is produced in interval training than in steady exercise stress. The removal mechanisms also have a specific maximum rate, and therefore in hard exercise stress more lactate is inevitably produced than removed. This results in a rapid rise in the lactate level of the body and exhaustion. The removal mechanisms of a fit person are efficient and quick to react. A lactate curve, where the amount of lactate is presented as a function of heart rate, represents in a way the condition of the person. The curve of an unfit person grows more evenly than that of a fit person. The lactate level of a fit person is relatively low up to a level of rather hard stress. At a given stress level, a lactate threshold, the curve rises steeply. This curve form can be explained by the fact that the lactate removal mechanisms of a fit person are effective and react rapidly to an elevated lactate production rate. The amount of lactate starts growing considerably only after reaching the maximal lactate removal rate. Correspondingly, the lactate removal mechanisms of an unfit person are weaker and follow with a minor delay the elevated lactate production rate. If the lactate curve is known, it is easy to plan exercise and recovery. Exercise should take place within the lactate curve area in which development is desired, because exercise improves blood circulation, among other things, and consequently the efficiency of the removal mechanisms.

At step 104 of FIG. 1, a neural network is trained with a large amount of user data. User data is advantageously collected, for instance, from about one thousand users, whereby the neural network learns and is able to set the weighting coefficients of synapses such that the model gives as good results as possible. At step 106, the neural network is fed with user-specific information, such as physiological parameters and exercise stress parameters. The model is advantageously calibrated prior to actual use by means of actual user data. For lactate, this means that the actual amount of lactate in blood is measured from blood a number of times during exercise, the obtained, actual measurement result is entered in the model, which calibrates the parameters of the model by means of feedback such that the actual measured value is obtainable by the model. As a result of the calibration, the model provides in actual use better and more accurate estimates on the amount of lactate in blood. In one preferred embodiment, the mathematical model is included in a heart rate monitor, the use phase of which is represented by method step 108. The heart rate monitor measures one or more heart rate parameters from the person's heart rate, on the basis of which parameters the heart rate monitor forms an assessment of the lactate concentration in the body. At step 110, the heart rate monitor advantageously displays the lactate concentration of blood on its display, for instance, to the user of the heart rate monitor, to a doctor or a trainer. Instead of or in addition to the display, the lactate concentration or a quantity representing the same, such as a person's exercise stress level, can be stored in the memory of the heart rate monitor for further processing. By means of the lactate concentration in the body it is possible to evaluate how an exercise session succeeded. An excessive lactate concentration may then indicate, for instance, that the workout/exercise was performed on an excessively high workload level. The lactate concentration can thus be used for controlling the workload level, for instance, such that the workload level is controlled in view of the running speed of an exercise performer or the resistance of an exercise bike. The lactate concentration is utilized for planning an exercise program, for instance, such that division of speed during exercise is adjusted on the basis of values provided by the lactate concentration.

Figure 2A:
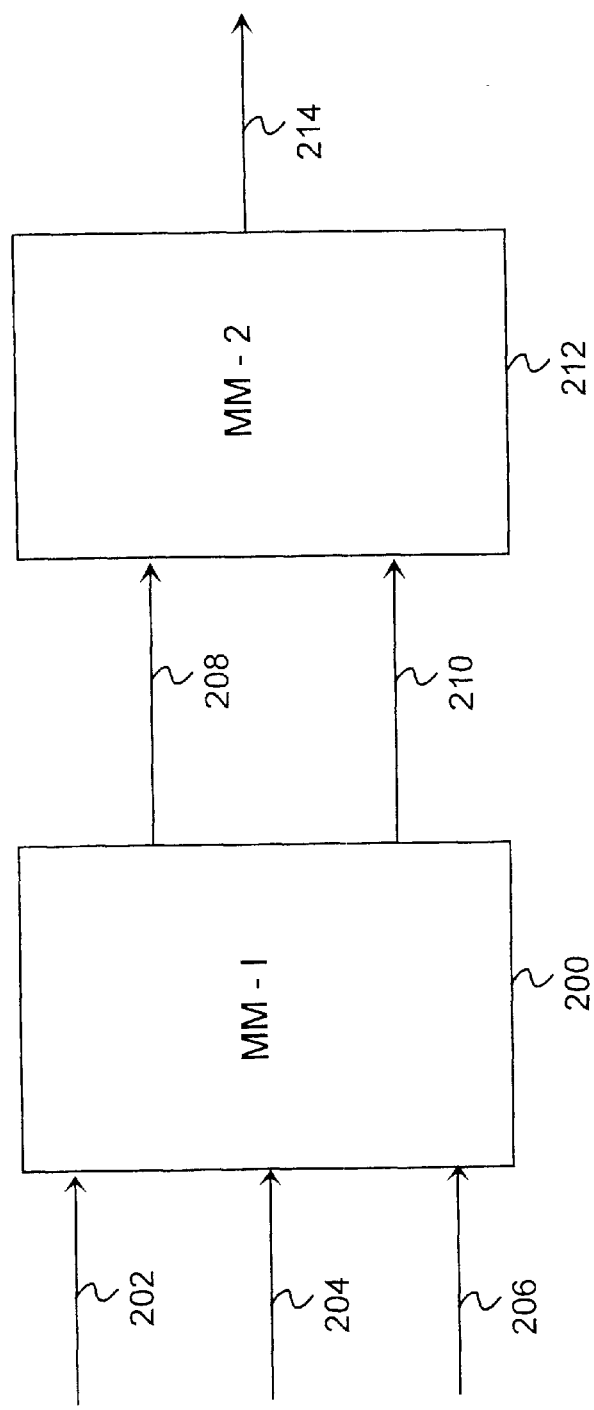
FIG. 2A shows a model structure of an embodiment of the invention.

In the following, the model will be described with reference to FIGS. 2A and 2B. FIG. 2 shows a preferred embodiment of the mathematical model which consists of a model structure comprising two sub-models 200, 212. It is obvious that the model can also comprise one or more than two sub-models. The first sub-model 200 of the model includes as input parameters one or more heart rate parameters 202 of the person, such as mean heart rate, standard deviation of the heart rate or the like. Further, the model includes as feeding data one or more stress parameters 204 representing the exercise stress, such as running speed or pedalling speed of the exercise bike. As the third input parameter set the model includes one or more physiological parameters 206 of the person, such as age, height, weight or gender. The above-described input parameter sets 204 to 206 are optional, i.e. they can be included in the model individually or simultaneously, or be omitted from the model. In one embodiment of the invention, the first part 200 of the model is implemented as a neural network that has been trained with user data comprising hundreds or even thousands of users. In one embodiment of the invention, the first part of the model outputs the person's stress level 208 during exercise. Output parameter set 210 represents one or more condition parameters provided by the model and describing the physical condition of the person, such as the maximal oxygen uptake or the fitness index.

The second part 212 of the model includes as input parameters information representing the stress level 208 of the above-described exercise, and optionally, one or more condition parameters 210 representing the condition of the user, which parameter is formed, like the stress level parameter, as a function of one or more heart rate parameters and advantageously also as a function of one or more optional parameters 204 to 206. In one preferred embodiment, the second sub-model 212 is a mathematically formed physiological model which gives the amount of lactate 214 in the person's body as an output parameter on the basis of the input parameters 208 to 210. The amount of lactate 214 is obtained as the output of the model. The second sub-model 212 is advantageously implemented as a neural network.

Figure 2B:
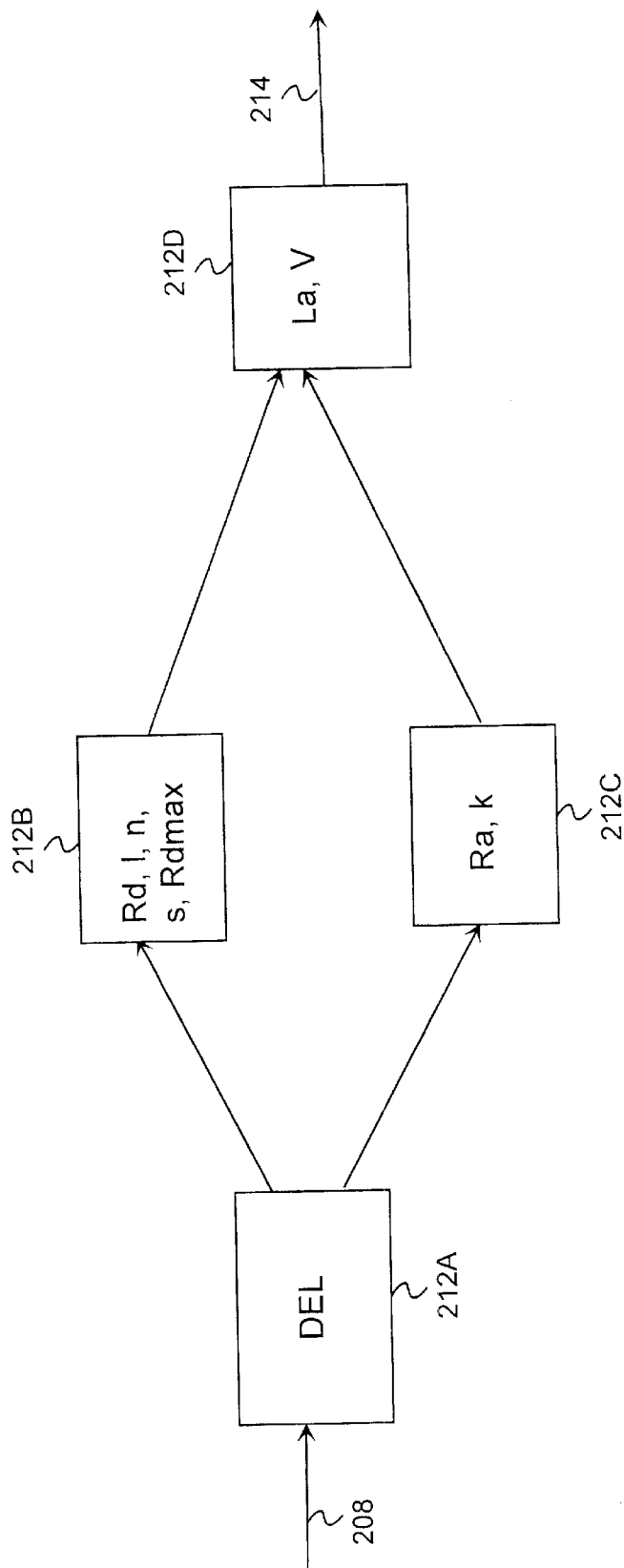
FIG. 2B shows a model structure of an embodiment of the invention.

The physiological base model of the second sub-model is described by means of an embodiment in FIG. 2B. The person's stress level 208 during exercise is entered in the model as an input. A delay unit 212A enables the presentation of the model in the form of a neural network according to one embodiment. Since the physiological model advantageously is in the form of a differential equation, a discrete form of the model can be implemented by a delay unit 212 that provides feedback. The physiological model with units 212B to 212D can be simply expressed by the equation (1)

$$\frac{d\,la(t)}{dt} = \frac{1}{V}[Ra(t) - Rd(t)] \quad (1)$$

where la(t) is the lactate concentration, Ra(t) is the production rate of lactate, Rd(t) the removing rate of lactate and V is the breakdown rate of lactate.

Figure 2C:
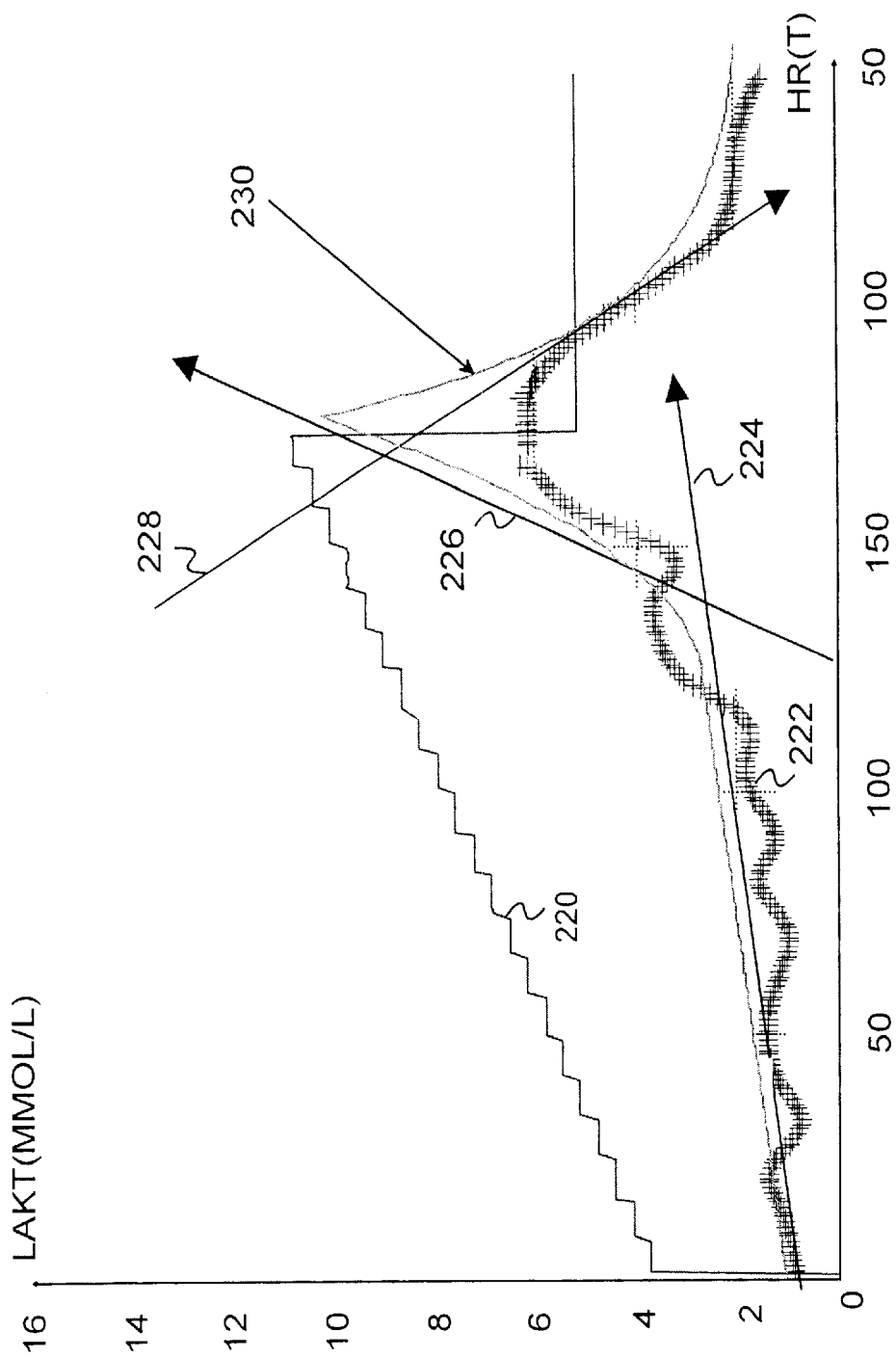
FIG. 2C shows the amount of lactate in the body as a function of progressive exercise.

The parameter k in the model represents the dependence of Ra on the stress level 208, l represents the dependence of Rd on the stress level, n represents the dependence of Rd on la and s represents the dependence of Rd on Rdmax. The maximal lactate removing rate is at the lactate threshold. FIG. 2C illustrates by way of example how the model is formed. In FIG. 2C, on the x-axis appears the person's heart rate as a function of time and progressive exercise, the unit being beat/minute, and on the y-axis appears the amount of lactate in blood, the unit being mmol/l. The curve 222 describes the measured amount of lactate and the curve 230 the lactate value given by the model. For forming the model, three straight lines and the slopes thereof are searched. The curve 224 describes the generating rate of lactate before the lactate threshold, which is at the intersection of the curves 224 and 226. The curve 226 describes the generating rate of lactate after exceeding the lactate threshold and the curve 228 the removing rate of lactate after the exercise, the exercise stress being described by the curve 220. The lactate threshold, which refers to the maximal removing rate of lactate, has a major importance in the model. Let us assume that persons having different fitness levels belong to different categories of lactate condition. In the lactate condition categories of fit persons the lactate threshold appears at a higher heart rate level and vice versa. In the model, the only function of the lactate threshold is to determine the heart rate value beyond which the amount of lactate increases faster than at a lower stress level/heart rate level.

Figure 3A:
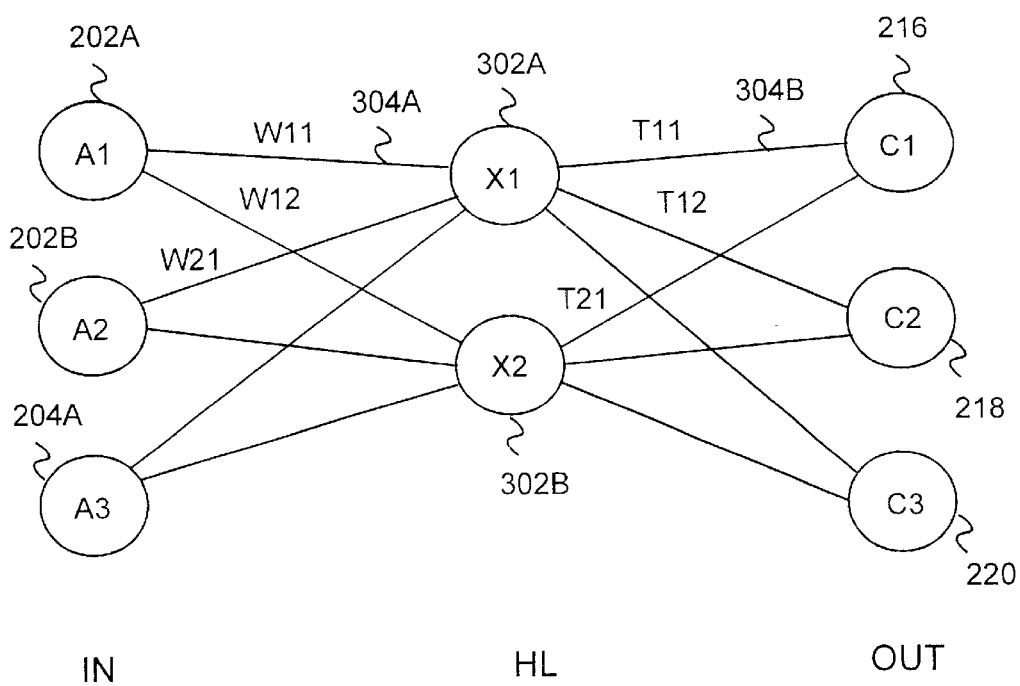
FIG. 3A illustrates the structure of a neural network.
Figure 3B:
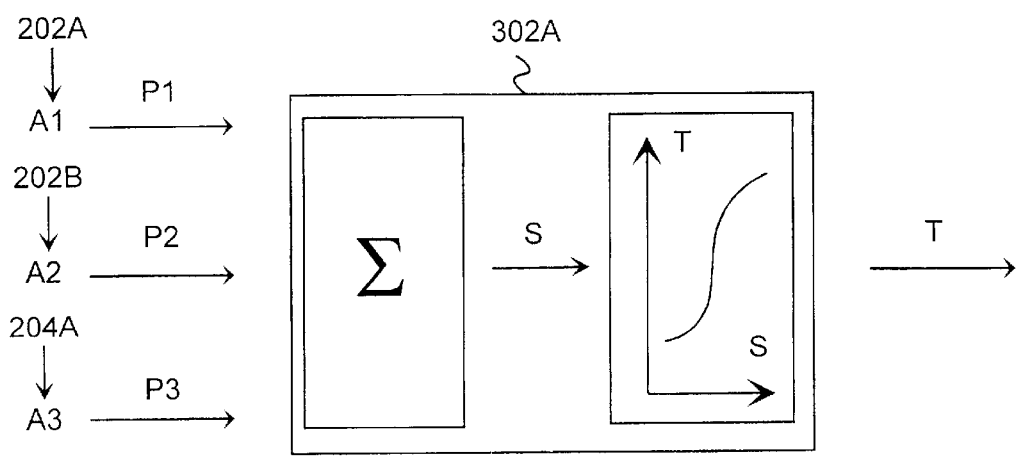
FIG. 3B illustrates the operation of the neural network.

In one embodiment of the invention, the mathematical model implementing the method of the invention is implemented as a neural network whose operational principle is described by FIGS. 3A and 3B. The neural network is a way to model complex applications, such as image and speech identification, applications in robotics and applications in medical analysis, the presentation of which is very difficult as a mathematical model. With reference to FIG. 2A, a neural network comprises neurons, for instance 202A to 202B, 302A to 302B, having a large number of interdependencies, for instance 304A to 304B. The interdependencies 304A to 304B of neurons are referred to as synapses, and a weighting coefficient, for instance W11, W12, is determined for each synapse. The neurons, i.e. nodes, can perform simple calculations, such as the neuron 302A calculating the sum weighted with weighting coefficients of the synapses of a previous layer. The neural network comprises at least an input layer, which includes the neurons 202A to 204A, and an output layer, which includes the neurons 216 to 220. As the performance of the two-layer neural network is rather limited, the neural network advantageously comprises at least one hidden layer HL, which includes the neurons 302A to 302B. There is no synapse between the neurons of the same layer, but the node has a synapse with all the neurons of the adjacent layers. FIG. 3B shows the structure of one neuron 302A in greater detail. The neuron 302A is inputted with respective input parameters 202A to 204A, weighted by weighting coefficients P1 to P3, for which input parameters the neuron forms a weighted sum S. The neuron enters the sum S in an activation function, which is typically a non-linear function of sigmoidal type. The neuron 302A outputs the final value T, and if said final value is delivered to the synapse 304B, it is multiplied by the weighting coefficient T11, whereas, if said final value is delivered to the node 218, it is multiplied by the weighting coefficient T12.

Training is an essential feature of the neural network. In a particular training phase, actual input and output values are presented to the model, and the model compares them with the calculated output values. A difference between the actual and calculated values, i.e. error, is processed in the model, which processing results in tuning the coefficients of the synapses so as to minimize the error. As a consequence of the training phase, the weight of significant synapses increases and the weight of less significant synapses becomes extremely low.

Figure 4A:
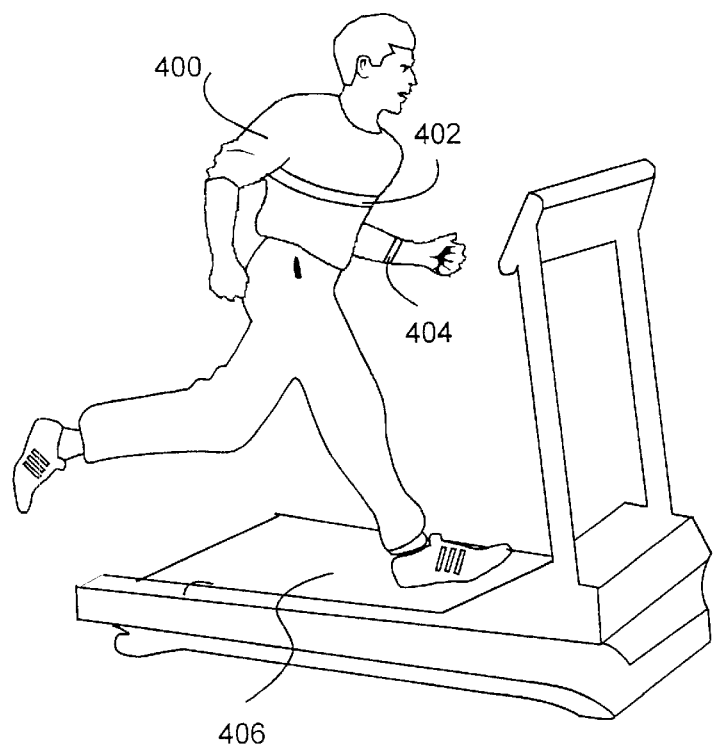
FIG. 4A shows a person performing an exercise.

FIG. 4A shows a person 400 who performs an exercise on a treadmill 406. The heart rate of the person 200 is measured by means of a transmitter electrode belt 402 fitted around the chest. Heart rate measuring is carried out by heart rate information measuring means which comprise, for instance, two or more electrodes 410A to 410B of the transmitter electrode belt 402, between which electrodes a difference of potential is created as the heart beats. The transmitter electrode belt 402 is fitted around the person's chest by means of, for instance, an elastic band made of elastic material. The measured heart rate is advantageously transmitted inductively to a wrist-worn receiver 404 which advantageously also comprises a display for displaying the measured heart rate. The invention is also applicable to heart rate monitors, in which the electrode belt 402 on the chest, in addition to measuring, also takes care of storing, processing and displaying the heart rate information, whereby there is no need for a separate receiver unit 404. The heart rate monitor can also be a single wrist-worn device, in which the transmitter part and the receiver part are integrated into one single device, whereby there is no need for transmitter and receiver electronics. The heart beat can be measured from the wrist, either from an ECG signal, arterial pressure pulse or by observing optically changes in the absorption or reflection of blood circulation. In the above cases the heart rate information measuring means are a pressure sensor or an optical measuring device.

Figure 4B:
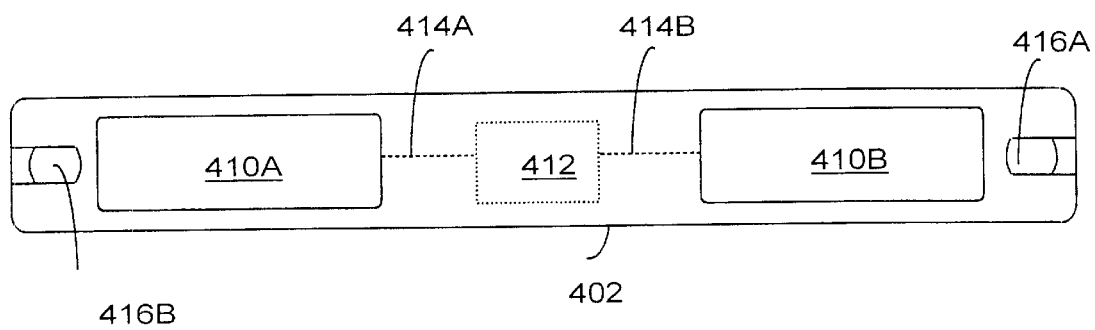
FIG. 4B shows an electrode belt according to an embodiment of the invention.

FIG. 4B shows the electrode belt 402 of FIG. 4A in greater detail. In FIG. 4B, the electrode belt 402 is depicted from the side of the electrodes 410A to 410B, i.e. from the side facing the body. The figure also shows securing means 416A to 416B, by which the electrode belt 402 can be secured to an elastic band to be fitted around the chest. In FIG. 4B, an electronic unit 412 for processing the heart rate information obtained from the electrodes 410A to 410B is depicted by a broken line. The electrodes 410A and 410B are coupled with conductors 414A and 414B to the electronic unit 412 respectively.

Figure 4C:
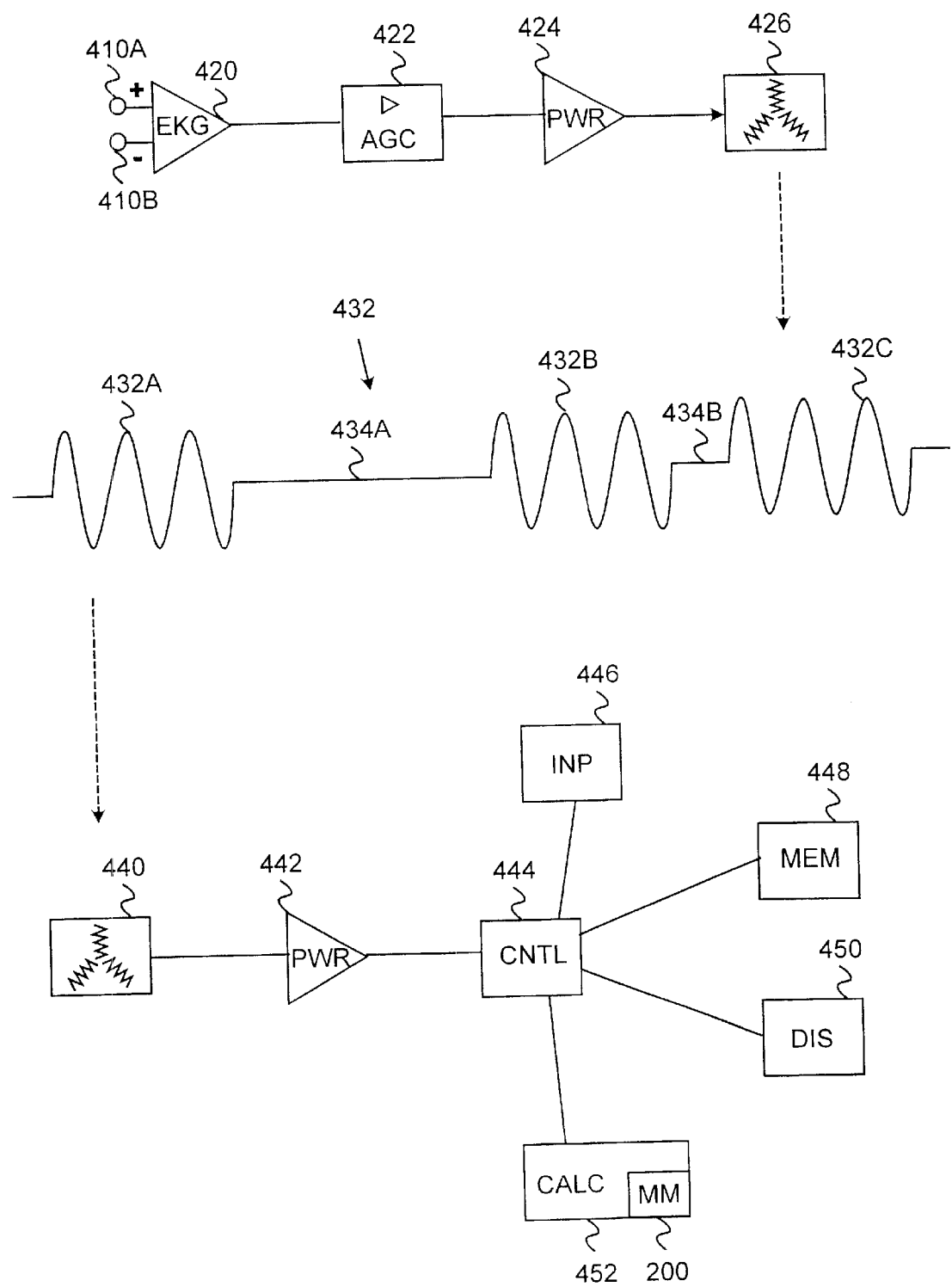
FIG. 4C shows a heart rate monitor arrangement according to an embodiment of the invention.

FIG. 4C depicts the structures of the transmitter electrode belt 402 and the receiver 404 by means of an embodiment. The topmost part of the figure depicts the transmitter electrode belt 402, the middle part depicts a sample of heart rate information to be transmitted and the bottom part depicts the receiver unit 404 in essence. The electronic unit 112 of the transmitter electrode belt 402 receives heart rate information from the means 410A to 410B for measuring one or more heart rate information parameters. The measuring means are advantageously electrodes which the heart rate monitor comprises at least two, but they can be more. From the electrodes the signal is applied to an ECG preamplifier 420 wherefrom the signal is transferred via an AGC amplifier 422 and a power amplifier 424 to a transmitter 426. The transmitter 426 is advantageously implemented as a coil which sends the heart rate information 430 inductively to a receiver, such as a wrist-worn receiver unit 404 or to an external computer, for instance.

One 5 kHz burst 432A corresponds to one heart beat, for instance, or a cluster of a plurality of bursts 432A to 432C may correspond to one beat. The intervals 432A to 432B of bursts 430A to 430C can be equal in length or mutually different in length, as appears in the situation of FIG. 4C. Information can be transmitted inductively, or alternatively, optically or via a conductor, for instance. The receiver 404, such as the wrist-worn receiver, comprises in one embodiment a receiver coil 440, from which the received signal is applied through a signal receiver 442 to a central processor 444, which coordinates the operation of different parts. Advantageously, the receiver 404 also comprises a memory 448 for storing the heart rate information and presenting means 450 for presenting the heart rate or the heart rate variables derived therefrom, such as the standard deviation. By the presenting means 450 it is also possible to display to the user information that is relevant in accordance with the method of the invention, such as the lactate concentration of the body, the value of a moving heart rate variation, the person's workload level or other corresponding information. The presenting means 450 comprise, for instance, a display, a speech controller or means for transmitting the heart rate and/or feedback information to an external computer or data network for presenting them separately from the heart rate monitor. The means for transmitting can be implemented, for instance, by an induction coil, an optical transmitter, or a connector for transmission via a connecting line. A heart rate measuring arrangement is in question if the information measured or generated by the heart rate monitor is transmitted to equipment outside the heart rate monitor, such as a computer. According to a preferred embodiment, the presenting means are then located in the computer, by which the information measured in real-time or stored in the memory 448 of the heart rate monitor can be displayed.

The heart rate monitor further comprises forming means for forming an assessment of the lactate concentration of the body on the basis of the heart rate. The forming means are advantageously implemented as the heart rate monitor's calculating unit 452 and the included mathematical model, which is a neural network, for instance. The forming means provide advantageous implementation of the method steps of the invention, in which the amounts of lactate and/or stress in the body are assessed by means of input parameters. It is clear that the calculating unit 542 need not be implemented as a separate device unit but that the calculating unit 452 and the mathematical model included therein can be part of the central processor 444. Further, it is clear that the heart rate monitor need not necessarily comprise the calculating unit as a separate device part but the model can be implemented in the central processor 444, for instance. The receiver 404 advantageously comprises entering means 446, such as a keypad or speech controller means. By the entering means 446 it is possible, for instance, to enter the physiological parameters and the exercise stress parameters required by the models.

In one preferred embodiment, the functions, means and models implementing the method steps of the invention are implemented by means of software in a general-purpose processor. Said means can also be implemented as ASIC, by separate logic components or by any corresponding known method.

In the embodiment of FIG. 4C the heart rate monitor refers to a whole formed by the transmitter electrode belt 402 and the receiver 404. In one embodiment, the heart rate monitor can also be implemented such that the above-described functions included in the transmitter electrode belt 402 and the receiver 404 are located in one device. Said one-piece device can be either such that is fitted on the chest for heart rate measurement, or alternatively, such that is worn on the wrist. It is obvious to a person skilled in the art that the electrode belt 402 and the receiver 404 may also comprise other parts than those depicted in FIGS. 4B and 4C, but it is not relevant to describe them in this connection.

Even though the invention is described above with reference to the examples of the attached drawings, it is obvious that the invention is not restricted thereto but it can be modified in a variety of ways within the scope of the inventive idea of the attached claims.

What is claimed is:

1. A method for assessing lactate concentration in a human body in connection with exercise, comprising measuring a person's heart rate information in the form of one or more heart rate parameters to be included in a mathematical model as input parameters and by forming, by means of a mathematical model which models the lactate concentration in the body, a lactate concentration level of the person's body as an output parameter of the model to be presented in the assessment of the lactate concentration of the body.

2. A method as claimed in claim 1, wherein by means of the heart rate information and at least one parameter representing the person's physiology the model provides an exercise stress level of the person for assessing the exercise stress level of the person in connection with exercise.

3. A method as claimed in claim 2, wherein the model provides an assessment of lactate concentration in the person's body by means of the person's exercise stress level.

4. A method as claimed in claim 2, wherein said physiological parameter is age, weight, height or gender.

5. A method as claimed in claim 1, wherein one or more exercise stress parameters representing the workload of the exercise are entered in the model as input parameters.

6. A method as claimed in claim 5, wherein the stress parameter is running speed, resistance of an exercise bike, velocity of a bicycle, resistance of a bicycle, swimming speed or activity.

7. A method as claimed in claim 1, wherein by means of one or more heart rate parameters and one or more physiological parameters the model provides one or more fitness variables representing the person's physical condition, which the model employs in the assessment of the lactate concentration in the person's body in connection with exercise.

8. A method as claimed in claim 1, wherein in the assessment of lactate amount the model employs lactate production rate in a muscle, lactate removal rate from the muscle and blood volume into which the lactate is dispersed.

9. A method as claimed in claim 1, wherein the mathematical model is a neural network.

10. A method as claimed in claim 9, wherein the neural network is trained on the basis of user information collected from a large number of users.

11. A method as claimed in claim 10, wherein in the neural network training the weighting coefficients between the neurons of the neural network are adjusted by means of feedback utilizing one or more output parameter values.

12. A method as claimed in claim 1, wherein the heart rate parameter is the rate representing the heart beat frequency, standard deviation of the heart rate, change rate of the heart rate or the like.

13. A method as claimed in claim 1, wherein the person's heart rate information is measured with a heart rate monitor.

14. A method as claimed in claim 1, wherein one or more input parameters are entered into the mathematical model included in the heart rate monitor with entering means of the heart rate monitor.

15. A method as claimed in claim 1, wherein the amount of lactate in the body is presented on the display of the heart rate monitor.

16. A method as claimed in claim 1, wherein the person's exercise stress level is presented on the display of the heart rate monitor.

17. A method as claimed in claim 16, wherein the exercise stress level is used for controlling the stress level of an exercise.

18. A method as claimed in claim 1, wherein lactate concentration during exercise are stored in the memory of the heart rate monitor to be used in post-exercise evaluation of the exercise performance.

19. A method as claimed in claim 18, wherein the exercise stress level is controlled as heart rate control, speed control or intensity control.

20. A heart rate measuring arrangement, comprising measuring means for measuring heart rate information, forming means for forming an assessment of the lactate concentration in the body on the basis of the heart rate information, presenting means for presenting the formed assessment of the amount of lactate in the body.

21. A heart rate measuring arrangement as claimed in claim 20, wherein the forming means are a calculating unit comprising a mathematical model which is arranged to receive as an input parameter one or more heart rate information parameters measured with the measuring means and to give as an output parameter the lactate concentration level of the human body to be presented by presenting means.

22. A heart rate measuring arrangement as claimed in claim 21, wherein the model included in the calculating unit is arranged to generate the person's exercise stress level by means of the heart rate information and at least one physiological parameter representing the person's physiology inputted in the model, which exercise stress level the model is arranged to use for forming the lactate concentration in the body.

23. A heart rate measuring arrangement as claimed in claim 21, wherein the model is arranged to apply as input parameters one or more exercise stress parameters representing the workload of an exercise.

24. A heart rate measuring arrangement as claimed in claim 23, wherein the exercise stress parameter is the running speed, resistance of an exercise bike or a corresponding variable.

25. A heart rate measuring arrangement as claimed in claim 23, wherein the mathematical model is a neural network.

26. A heart rate measuring arrangement as claimed in claim 25, wherein the neural network is trained on the basis of user information collected from a large number of users.

27. A heart rate measuring arrangement as claimed in claim 26, wherein in the neural network training weighting coefficients between the neurons in the neural network are adjusted by means of feedback utilizing one or more output parameter values.

28. A heart rate measuring arrangement as claimed in claim 21, wherein, by means of one or more heart rate parameters and one or more physiological parameters included in the model as input parameters, the model is arranged to generate one or more fitness variables representing the user's physical condition, by which variables the model is arranged to assess the lactate concentration in the person's body in connection with exercise.

29. A heart rate measuring arrangement as claimed in claim 28, wherein the physiological parameter is age, gender, height, weight or a like parameter representing the person's physiological property.

30. A heart rate measuring arrangement as claimed in claim 21, wherein in the assessment of the lactate amount the model is arranged to employ the production rate of lactate in a muscle, removal rate of lactate from the muscle and blood volume into which the lactate is dispersed.

31. A heart rate measuring arrangement as claimed in claim 21, wherein the heart rate parameter is a parameter representing the heart beat frequency, the standard deviation of the heart rate or the like.

32. A heart rate measuring arrangement as claimed in claim 21, comprising entering means for entering one or more input parameters into the mathematical model.

33. A heart rate measuring arrangement as claimed in claim 20, comprising a memory for storing the heart rate information and/or the information generated in the calculating unit.

34. A heart rate measuring arrangement as claimed in claim 20, wherein the measuring means are an electrode belt for measuring the heart rate, the heart rate measuring arrangement further comprising a receiver unit which comprises a receiver for receiving the heart rate information transmitted from a transmitter included in the electrode belt, the receiver unit further comprising said presenting means.

35. A heart rate measuring arrangement as claimed in claim 34, wherein the presenting means are a display of the receiver unit.

36. A heart rate measuring arrangement as claimed in claim 20, wherein the heart rate measuring arrangement is a one-piece wrist-worn heart rate monitor which comprises one or more sensors for measuring the heart rate and a calculating unit, said presenting means being the display of the heart rate monitor for presenting the lactate concentration in the body.

37. A heart rate measuring arrangement as claimed in claim 20, wherein the heart rate measuring arrangement is arranged to employ the lactate concentration in the body for assessing a sufficient duration of post-exercise recovery session.

* * * * *